US011300577B1

(12) United States Patent
Jones et al.

(10) Patent No.: US 11,300,577 B1
(45) Date of Patent: Apr. 12, 2022

(54) TURBIDITY NORMALIZATION ALGORITHM AND METHODS OF REDUCING INTRALIPID/LIPEMIA INTERFERENCE IN HEMOGLOBIN A1C ASSAYS

(71) Applicant: Siemens Healthcare Diagnostics Inc., Tarrytown, NY (US)

(72) Inventors: Justin Jones, Middletown, DE (US); Jian Dai, Newark, DE (US); Candice Robinson, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/310,033

(22) PCT Filed: Nov. 15, 2019

(86) PCT No.: PCT/US2019/061612
§ 371 (c)(1),
(2) Date: Jul. 13, 2021

(87) PCT Pub. No.: WO2020/159599
PCT Pub. Date: Aug. 6, 2020

Related U.S. Application Data

(60) Provisional application No. 62/798,158, filed on Jan. 29, 2019.

(51) Int. Cl.
*G01N 33/72* (2006.01)
*G01N 21/31* (2006.01)

(52) U.S. Cl.
CPC ......... *G01N 33/723* (2013.01); *G01N 21/314* (2013.01); *G01N 2021/3148* (2013.01)

(58) Field of Classification Search
None
See application file for complete search history.

(56) References Cited

U.S. PATENT DOCUMENTS

| 4,200,435 A | 4/1980 | Stroupe et al. |
| 4,997,769 A | 3/1991 | Lundsgaard |
| (Continued) | | |

FOREIGN PATENT DOCUMENTS

| CN | 1220007 | 6/1999 |
| CN | 102564983 | 7/2012 |
| (Continued) | | |

OTHER PUBLICATIONS

Zhou, Wen-Juan et al: "Standardization and Technology Development of Measurement of Glycated Human Hemoglobin"; Progress in Biochemistry and Biophysics; vol. 42, No. 5; Mar. 23, 2015; pp. 443-456; DOI: 10.16476/j.pibb.2014.0281 / Mar. 23, 2015 English language abstract only.

(Continued)

*Primary Examiner* — Shawn Decenzo

(57) ABSTRACT

A method of spectroscopically measuring percent glycated hemoglobin or a glycated hemoglobin:total hemoglobin ratio in a biological sample is disclosed. The method includes the use of a turbidity normalization algorithm to normalize the total hemoglobin concentration calculated from the spectroscopic measurements to substantially remove any turbidity interference therefrom. The turbidity normalization eliminates the negative bias observed with intralipid/lipemia and thus provides a glycated hemoglobin assay with no significant interference from intralipid/lipemia.

17 Claims, 6 Drawing Sheets

(56) References Cited

U.S. PATENT DOCUMENTS

| | | | | |
|---|---|---|---|---|
| 5,470,759 | A | * 11/1995 | Sugiyama | G01N 33/723 |
| | | | | 436/66 |
| 5,674,699 | A | * 10/1997 | Saunders | G01N 33/582 |
| | | | | 435/7.1 |
| 2009/0317912 | A1 | * 12/2009 | Sugiyama | G01N 30/88 |
| | | | | 436/67 |
| 2010/0291691 | A1 | * 11/2010 | Sugiyama | G01N 30/74 |
| | | | | 436/67 |
| 2013/0252262 | A1 | * 9/2013 | Srinivasan | G01N 33/54326 |
| | | | | 435/7.1 |
| 2014/0192342 | A1 | 7/2014 | Sass et al. | |
| 2014/0370539 | A1 | 12/2014 | Shen et al. | |
| 2019/0169674 | A1 | 6/2019 | Machida et al. | |
| 2021/0270849 | A1 | * 9/2021 | Wei | G01N 33/541 |

FOREIGN PATENT DOCUMENTS

| | | |
|---|---|---|
| CN | 103649721 | 3/2014 |
| CN | 104105968 | 10/2014 |
| CN | 105823739 | 8/2016 |
| CN | 107807024 | 3/2018 |
| JP | 2018533012 | 11/2018 |
| JP | 2020008578 | 1/2020 |
| WO | 2018030531 | 2/2018 |
| WO | 2018093573 | 5/2018 |

OTHER PUBLICATIONS

Sehgal, L. R et al: "Effect of intralipid on measurements of total hemoglobin and oxyhemoglobin in whole blood"; Critical care medicine; vol. 12, No. 10, (1984).

International Search Report for PCT/US2019/061612 dated Jan. 28, 2020.

Farrel, L. Christopher-John et al: "Serum indices: managing assay interference"; Annals of Clinical Biochemistry; vol. 53, No. 5, Sep. 1, 2016 (Sep. 1, 2016), pp. 527-538.

* cited by examiner

US 11,300,577 B1

TURBIDITY NORMALIZATION ALGORITHM AND METHODS OF REDUCING INTRALIPID/LIPEMIA INTERFERENCE IN HEMOGLOBIN A1C ASSAYS

CROSS REFERENCE TO RELATED APPLICATIONS/INCORPORATION BY REFERENCE STATEMENT

Not Applicable.

STATEMENT REGARDING FEDERALLY SPONSORED RESEARCH OR DEVELOPMENT

Not Applicable.

BACKGROUND

Hemoglobin present in red blood cells can be glycated by the non-enzymatic addition of a glucose molecule to the amino terminus of the β-chain of the hemoglobin. Once a hemoglobin molecule is glycated, it remains glycated, and an accumulation of glycated hemoglobin within a red cell reflects the average level of glucose to which the cell has been exposed during its life cycle. The level of glycated hemoglobin present in an individual's blood is thus proportional to the level of glucose in the blood and is an indicator of the individual's mean daily blood glucose concentration over the previous four weeks to three months. The ratio of glycated hemoglobin to total hemoglobin in a whole blood sample is therefore quite useful in the diagnosis and monitoring of patients with diabetes mellitus.

Accurate control of blood glucose can ameliorate much of the morbidity and mortality associated with diabetes mellitus. Therefore, many different assays for hemoglobin have been developed, based on the physical and chemical properties of hemoglobin or based on specific antibody-recognized epitopes thereof. Clinical studies have shown that HbA1c results improve decision making, patient compliance, and outcomes (Thaler et al. (1999) *Diabetes Care*, 22:1415-1421; and Miller et al. (2003) *Diabetes Care*, 26:1158-1163).

Glycated hemoglobin (HbA1c) is formed by the non-enzymatic glycation of the N-terminus of the β-chain of hemoglobin A. Measurement of HbA1c is used as an aid in the diagnosis and monitoring of long-term blood glucose control in patients with diabetes mellitus, and as an aid in the identification of patients at risk for developing diabetes mellitus. The HbA1c level reflects the mean glucose concentration over the previous period (approximately 8-12 weeks, depending on the individual) and provides a better indication of long-term glycemic control than blood and urinary glucose determinations. Studies have shown that long term control of HbA1c levels can decrease the risk for development and progression of chronic complications caused by diabetes.

Immunoassays are currently the most common type of hemoglobin assay methods used in the clinical laboratory setting. These immunoassays utilize antibodies that recognize an epitope of hemoglobin, and in particular instances, an epitope of glycated hemoglobin (HbA1c), such as (but not limited to) at least a portion of the N-terminal glycated amino acids thereof. For example, the turbidimetric inhibition immunoassay (TINIA) for the analyte HbA1c utilizes an anti-HbA1c antibody and a polyhapten agglutinator (i.e., a synthetic molecule that contains multiple HbA1c epitopes to cause agglutination with free antibody). However, incompletely dispersed polyhapten reagent is a major interferent in this assay, as it essentially mimics the insoluble antibody-polyhapten complex; incompletely dispersed polyhapten reagent causes light scattering that is subsequently measured turbidimetrically and thus translated into falsely low HbA1c values due to the inverse relationship between absorbance and analyte concentration.

Spectroscopic methods are also utilized for hemoglobin assays; however, the presence of lipids within the biological samples can cause interference at one or more of the wavelengths utilized in these methods. Thus, there is a need for new and improved hemoglobin A1c assays that utilize spectroscopic methods and for which no significant interference from intralipid/lipemia is observed.

DETAILED DESCRIPTION

Figure 1:
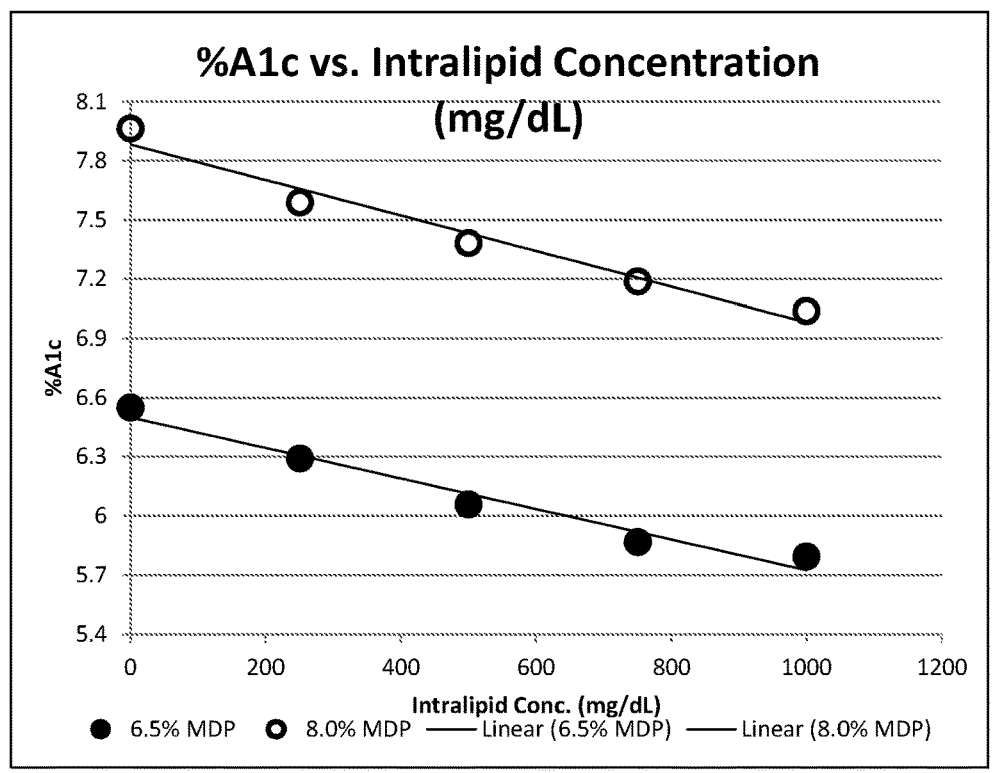
FIG. 1 graphically illustrates percent glycated hemoglobin (% A1c) versus intralipid concentration (mg/dL) results obtained on Atellica CH clinical chemistry analyzer (Siemens Healthineers, Tarrytown, N.Y.) with whole blood samples spiked with intralipid.

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. (Molecular Cloning: A Laboratory Manual, $2^{nd}$ ed., Cold Spring Harbor Laboratory Press, Cold Spring Harbor, N.Y. (1989)) and Coligan et al. (Current Protocols in Immunology, Wiley Interscience (1994)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions, kits, and/or methods disclosed herein can be made and executed without undue experimentation in light of the present disclosure. While the compositions, kits, and/or methods have been described in terms of particular embodiments, it will be apparent to those of skill in the art that variations may be applied to the compositions, kits, and/or methods and in the steps or in the sequence of steps of the methods described herein without departing from the concept, spirit, and scope of the present disclosure. All such similar substitutes and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "sample" as used herein will be understood to include any type of biological sample that may be utilized in accordance with the present disclosure. Examples of fluidic biological samples that may be utilized include, but are not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "reaction cuvette" as used herein includes any device(s) capable of performing at least one diagnostic assay as described herein. The reaction cuvette may perform the diagnostic assay(s) manually, but, in most instances, the reaction cuvette will be inserted into a system that automates the performance of the diagnostic assay(s). In one non-limiting embodiment, the reaction cuvette comprises a reaction cuvette for use in automated diagnostic assays conducted by, for example but not by way of limitation, Atellica clinical chemistry systems commercially available from Siemens Healthineers (Tarrytown, N.Y.). However, it will be understood that the reaction cuvette can be any commercially available product or cuvette described or otherwise contemplated herein that is capable of performing one or more diagnostic assays in accordance with the present disclosure.

Turning now to the presently disclosed and/or claimed inventive concepts, certain non-limiting embodiments of the present disclosure relate generally to methods for reducing interference in hemoglobin A1c assays, wherein the interference is caused (for example but not by way of limitation) by intralipid/lipemia, and wherein the interference is reduced through the use of a turbidity normalization algorithm. In particular, certain non-limiting embodiments of the present disclosure are directed to glycated hemoglobin assays in which any turbidity interference has been substantially removed therefrom; for example (but not by way of limitation), any turbidity interference may be substantially reduced to less than +/−about 5% at an intralipid concentration of up to about 1000 mg/dL. In this manner, any negative bias observed with intralipid/lipemia is removed from the assay.

Certain non-limiting embodiments of the present disclosure are directed to a method of measuring percent glycated hemoglobin or a glycated hemoglobin:total hemoglobin ratio in a biological sample. The method includes the steps of: (i) measuring absorbance at a first wavelength and a second wavelength in a biological sample containing lysed red blood cells and determining a total hemoglobin concentration (tHb) based on the measurements obtained at these two wavelengths, wherein the first wavelength is 658 nm, and wherein the second wavelength is in a range of from about 689 nm to about 699 nm; (ii) measuring absorbance at a third wavelength and a fourth wavelength in the biological sample containing lysed red blood cells and determining a glycated hemoglobin concentration (A1c) based on the measurements obtained at these two wavelengths, wherein the third wavelength is 658 nm, and wherein the fourth wavelength is in a range of from about 785 nm to about 825 nm; (iii) normalizing the total hemoglobin concentration calculated in (i) utilizing the absorbance measured at the fourth wavelength (cHb) in step (ii) and a turbidity normalization algorithm to substantially remove any turbidity interference from the wavelength measurements of (i), wherein any turbidity interference is substantially reduced to less than +/−about 5% at an intralipid concentration of up to about 1000 mg/dL, and wherein the turbidity normalization algorithm is: Normalized tHb=1.03×tHb (µmol/L)−cHb× 0.7899; and (iv) calculating a percent glycated hemoglobin or glycated hemoglobin:total hemoglobin ratio based on the concentrations calculated in (ii) and (iii).

In certain non-limiting embodiments of the above method, the biological sample is a lysed whole blood sample.

In certain non-limiting embodiments of the above method, the steps are performed in a single reaction cuvette.

The second wavelength may be any integer within the range of from about 689 nm to about 699 nm, including about 689 nm, about 690 nm, about 691 nm, about 692 nm, about 693 nm, about 694 nm, about 695 nm, about 696 nm, about 697 nm, about 698 nm, and about 699 nm. In a particular (but non-limiting) embodiment, the second wavelength is 694 nm.

The fourth wavelength may be any integer within the range of from about 785 nm to about 825 nm, including about 785 nm, about 786 nm, about 787 nm, about 788 nm, about 789 nm, about 790 nm, about 791 nm, about 792 nm, about 793 nm, about 794 nm, about 795 nm, about 796 nm, about 797 nm, about 798 nm, about 799 nm, about 800 nm, about 801 nm, about 802 nm, about 803 nm, about 804 nm, about 805 nm, about 806 nm, about 807 nm, about 808 nm, about 809 nm, about 810 nm, about 811 nm, about 812 nm, about 813 nm, about 814 nm, about 815 nm, about 816 nm, about 817 nm, about 818 nm, about 819 nm, about 820 nm, about 821 nm, about 822 nm, about 823 nm, about 824 nm, and about 825 nm. In a particular (but non-limiting) embodiment, the fourth wavelength is 805 nm.

Certain non-limiting embodiments of the present disclosure are directed to a method of measuring percent glycated hemoglobin or a glycated hemoglobin:total hemoglobin ratio in a biological sample. The method includes the steps of: (a) lysing red blood cells present in the biological sample; (b) reacting the lysed red blood cells with a reagent to oxidize hemoglobin to methemoglobin; (c) cleaving an N-terminal fructosyl dipeptide fragment from the hemoglobin beta chain with a protease; (d) converting methemoglobin into azide-methemoglobin; (e) measuring absorbance at a first wavelength and a second wavelength and determining a total hemoglobin concentration (tHb) based on the measurements obtained at these two wavelengths, wherein the first wavelength is 658 nm, and wherein the second wavelength is in a range of from about 689 nm to about 699 nm; (f) reacting the N-terminal fructosyl peptide fragment with a reagent to generate hydrogen peroxide; (g) measuring absorbance at a third wavelength and a fourth wavelength and determining a glycated hemoglobin concentration (A1c) based on the measurements obtained at these two wavelengths, wherein the third wavelength is 658 nm, and wherein the fourth wavelength is in a range of from about 785 nm to about 825 nm; (h) normalizing the total hemoglobin concentration calculated in step (e) utilizing the absorbance measured at the fourth wavelength (cHb) in step (g) and a turbidity normalization algorithm to substantially remove any turbidity interference from the wavelength measurements of step (e); and (i) calculating a percent glycated hemoglobin or glycated hemoglobin:total hemoglobin ratio based on the concentrations calculated in (g) and (h).

In certain non-limiting embodiments, the turbidity normalization algorithm used in step (h) is:

Normalized tHb=1.03×tHb (μmol/L)−cHb×0.7899.

In certain non-limiting embodiments, any turbidity interference is substantially reduced to less than +/−about 5% at an intralipid concentration of up to about 1000 mg/dL.

In certain non-limiting embodiments, all of the steps (a)-(g) of the method are performed in a single reaction cuvette.

The second wavelength may be any integer within the range of from about 689 nm to about 699 nm, including about 689 nm, about 690 nm, about 691 nm, about 692 nm, about 693 nm, about 694 nm, about 695 nm, about 696 nm, about 697 nm, about 698 nm, and about 699 nm. In a particular (but non-limiting) embodiment, the second wavelength is 694 nm.

The fourth wavelength may be any integer within the range of from about 785 nm to about 825 nm, including about 785 nm, about 786 nm, about 787 nm, about 788 nm, about 789 nm, about 790 nm, about 791 nm, about 792 nm, about 793 nm, about 794 nm, about 795 nm, about 796 nm, about 797 nm, about 798 nm, about 799 nm, about 800 nm, about 801 nm, about 802 nm, about 803 nm, about 804 nm, about 805 nm, about 806 nm, about 807 nm, about 808 nm, about 809 nm, about 810 nm, about 811 nm, about 812 nm, about 813 nm, about 814 nm, about 815 nm, about 816 nm, about 817 nm, about 818 nm, about 819 nm, about 820 nm, about 821 nm, about 822 nm, about 823 nm, about 824 nm, and about 825 nm. In a particular (but non-limiting) embodiment, the fourth wavelength is 805 nm.

In certain non-limiting embodiments, the biological sample is a whole blood sample.

Any lysing reagent known in the art or otherwise contemplated herein may be utilized to lyse the red blood cells present in the biological sample in accordance with the present disclosure. Lysing reagents are well known in the art and widely available commercially, and therefore no further discussion thereof is deemed necessary.

Any reagent known in the art capable of oxidizing hemoglobin to methemoglobin in the methods disclosed herein may be utilized in accordance with the present disclosure. In certain non-limiting embodiments, the reagent used to oxidize hemoglobin to methemoglobin in step (b) is sodium nitrite.

Any azide capable of converting methemoglobin into azide-methemoglobin in step (d) of the methods disclosed herein may be utilized in accordance with the present disclosure. In certain non-limiting embodiments, methemoglobin is converted into azide-methemoglobin in the presence of sodium azide.

Any reagent capable of resulting in the generation of hydrogen peroxide upon reaction with the N-terminal fructosyl peptide fragment of the hemoglobin beta chain in step (f) of the methods disclosed herein may be utilized in accordance with the present disclosure. In certain non-limiting embodiments, the reagent used in step (f) is fructosyl peptide oxidase.

Certain non-limiting embodiments of the present disclosure are directed to a method of measuring percent glycated hemoglobin or a glycated hemoglobin:total hemoglobin ratio in a biological sample. The method comprises the steps of: (a) lysing red blood cells present in the biological sample; (b) reacting the lysed red blood cells with sodium nitrite to oxidize hemoglobin to methemoglobin; (c) cleaving an N-terminal fructosyl dipeptide fragment from the hemoglobin beta chain with a protease; (d) converting methemoglobin into azide-methemoglobin in the presence of sodium azide; (e) measuring absorbance at a first wavelength and a second wavelength and determining a total hemoglobin concentration (tHb) based on the measurements obtained at these two wavelengths, wherein the first wavelength is 658 nm, and wherein the second wavelength is in a range of from about 689 nm to about 699 nm; (f) reacting the N-terminal fructosyl peptide fragment with a reagent to generate hydrogen peroxide; (g) measuring absorbance at a third wavelength and a fourth wavelength and determining a glycated hemoglobin concentration (A1c) based on the measurements obtained at these two wavelengths, wherein the third wavelength is 658 nm, and wherein the fourth wavelength is in a range of from about 785 nm to about 825 nm; (h) normalizing the total hemoglobin concentration calculated in step (e) utilizing the absorbance measured at the fourth wavelength (cHb) in step (g) and a turbidity normalization algorithm to substantially remove any turbidity interference from the wavelength measurements of (e), wherein any turbidity interference is substantially reduced to less than +/−about 5% at an intralipid concentration of up to about 1000 mg/dL, and wherein the turbidity normalization algorithm is: Normalized tHb=1.03×tHb (μmol/L)−cHb X 0.7899; and (i) calculating a percent glycated hemoglobin or glycated hemoglobin:total hemoglobin ratio based on the concentrations calculated in (g) and (h).

In certain non-limiting embodiments of the above method, the biological sample is a whole blood sample.

In certain non-limiting embodiments of the above method, steps (a)-(g) are performed in a single reaction cuvette.

The second wavelength may be any integer within the range of from about 689 nm to about 699 nm, including about 689 nm, about 690 nm, about 691 nm, about 692 nm, about 693 nm, about 694 nm, about 695 nm, about 696 nm, about 697 nm, about 698 nm, and about 699 nm. In a particular (but non-limiting) embodiment, the second wavelength is 694 nm.

The fourth wavelength may be any integer within the range of from about 785 nm to about 825 nm, including about 785 nm, about 786 nm, about 787 nm, about 788 nm, about 789 nm, about 790 nm, about 791 nm, about 792 nm, about 793 nm, about 794 nm, about 795 nm, about 796 nm, about 797 nm, about 798 nm, about 799 nm, about 800 nm, about 801 nm, about 802 nm, about 803 nm, about 804 nm, about 805 nm, about 806 nm, about 807 nm, about 808 nm, about 809 nm, about 810 nm, about 811 nm, about 812 nm, about 813 nm, about 814 nm, about 815 nm, about 816 nm, about 817 nm, about 818 nm, about 819 nm, about 820 nm, about 821 nm, about 822 nm, about 823 nm, about 824 nm, and about 825 nm. In a particular (but non-limiting) embodiment, the fourth wavelength is 805 nm.

Examples

An Example is provided hereinbelow. However, the present disclosure is to be understood to not be limited in its application to the specific experimentation, results, and laboratory procedures disclosed herein. Rather, the Example is simply provided as one of various embodiments and is meant to be exemplary, not exhaustive.

The currently used glycated hemoglobin assay (developed for the Advia clinical chemistry analyzer; Siemens Healthineers, Tarrytown, N.Y.) consists of two separate measurements: glycated hemoglobin (A1c_E) and total hemoglobin (tHb_E). The two measurements are used to determine the % HbA1c (NGSP units) or the hemoglobin A1c_E/tHb_E ratio in mmol/mol (IFCC units).

The anticoagulated whole blood specimen is lysed on the system for the automated assay or may be lysed manually using a pretreatment solution to obtain hemolysate for a manual assay.

This glycated hemoglobin assay is an enzymatic method that specifically measures N-terminal fructosyl dipeptides on the beta-chain of HbA1c. In the pretreatment step, the erythrocytes are lysed, and the hemoglobin is oxidized to methemoglobin by reaction with sodium nitrite. In the first step of the reaction, the N-terminal fructosyl dipeptide fragment is cleaved from the hemoglobin beta chain with a protease. Concurrently, methemoglobin is converted into stable azide-methemoglobin in the presence of sodium azide, and the total hemoglobin concentration is determined by measuring the absorbance at 478/805 nm. In the second step of the reaction, fructosyl peptide oxidase (FPDX) is added to react with the fructosyl dipeptide to generate hydrogen peroxide. The hydrogen peroxide reacts with the chromogen in the presence of peroxidase to develop a color that is measured at 658/805 nm.

This glycated hemoglobin assay also incorporates a turbidity normalization mechanism (cHb_E) that is measured at 884 nm to effectively remove any sample turbidity which could impact the tHb_E measurement.

However, other clinical chemistry analyzers do not have a filter at the wavelength used for the turbidity normalization component of the above-described assay (884 nm); therefore, other normalization methods must be developed to allow these clinical chemistry analyzers to perform glycated hemoglobin assays that include a turbidity normalization component. As described herein below, it has been found that the glycated hemoglobin assays described herein remove any significant interference from intralipid/lipemia.

Turning now to the glycated hemoglobin assay of the present disclosure, this assay is also an enzymatic endpoint assay where the result is measured as a percent of two parameters: A1c, measured at 658/805 nm, and total hemoglobin (tHb), measured at 478/694 nm. The assay further includes the incorporation of a third subparameter, cHb, to normalize falsely elevated tHb values in samples with intralipid interference and/or high turbidity.

In contrast to the assay developed for the Advia clinical chemistry analyzer described herein above, in the current glycated hemoglobin assay, cHb is measured during the same read cycles as tHb at 805 nm where absorbance is independent of intralipid interference or increased turbidity. The following normalization equation is employed in the glycated hemoglobin assay disclosed herein:

$$\text{Normalized tHb\_}E = 1.055 \times \text{tHb} \, (\mu\text{mol/L}) - \text{cHb} \, (\text{Abs}_{884\,nm}) \times 1400.$$

Samples with intralipid or increased turbidity were tested on the two different clinical chemistry analyzers (Atellica CH and Advia modules, Siemens Healthineers, Tarrytown, N.Y.) and were found to behave similarly on both platforms. In absence of turbidity normalization, these samples exhibit falsely elevated tHb values and consequently falsely decreased HbA1c (%) values (FIG. 1).

Figure 2:
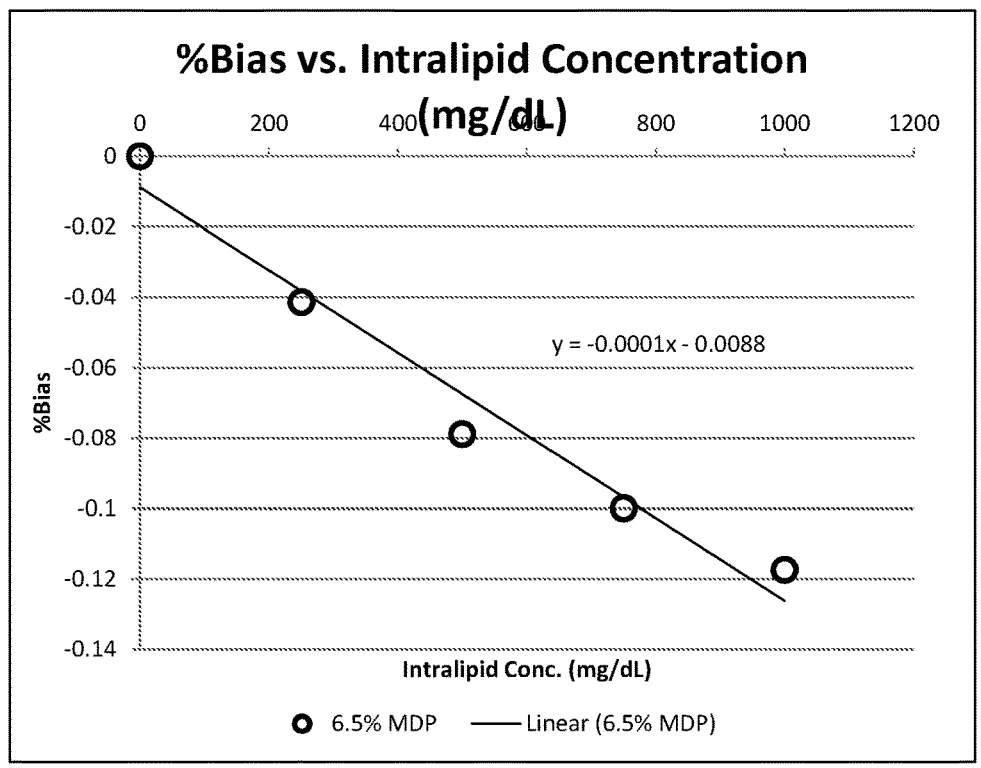
FIG. 2 graphically illustrates % Bias versus intralipid concentration (mg/dL) results obtained with whole blood (6.5% HbA1c) spiked with intralipid.
Figure 3:
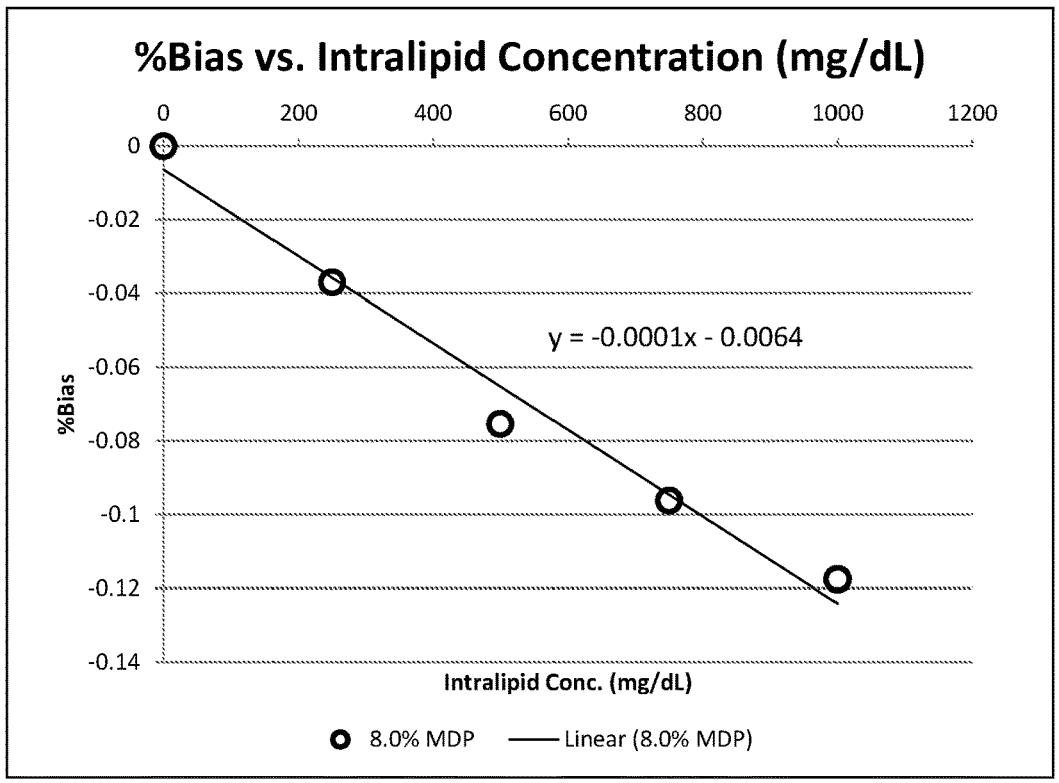
FIG. 3 graphically illustrates % Bias versus intralipid concentration (mg/dL) results obtained with whole blood (8.0% HbA1c) spiked with intralipid.

When spiked with intralipid, whole blood samples fail the |+/−5%| bias specification. When calculated to the target |+/−5%| bias, a passing sample only has approximately 300 mg/dL of intralipid, which is well below the 1000 mg/dL intralipid target concentration (FIG. 2 and FIG. 3 and Table I).

TABLE I

Atellica CH-Intralipid Spiked Samples Without Normalization Without Normalization

| MDP (% A1c) | Intralipid Conc (mg/dL) | Mean (% A1c) | Intralipid % Bias |
|---|---|---|---|
| 6.5% | 0 | 6.55 | |
| | 250 | 6.29 | −4% |
| | 500 | 6.06 | −8% |
| | 750 | 5.87 | −10% |
| | 1000 | 5.79 | −12% |
| 8.5% | 0 | 7.96 | |
| | 250 | 7.59 | −5% |
| | 5000 | 7.38 | −7% |
| | 750 | 7.19 | −10% |
| | 1000 | 7.04 | −12% |

Figure 4:
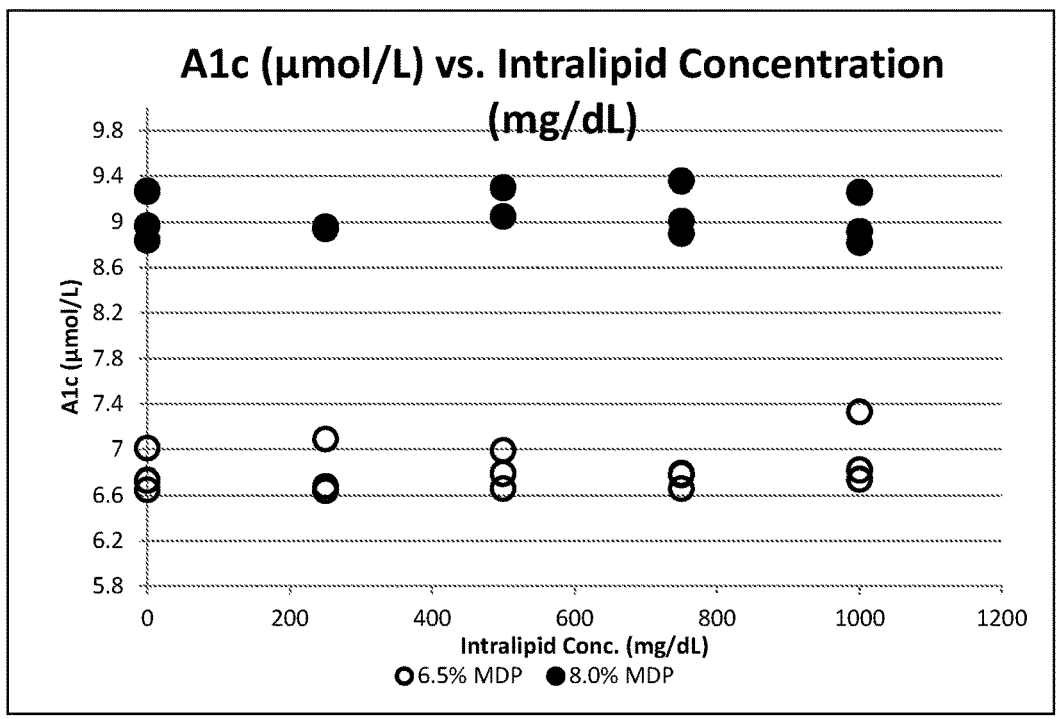
FIG. 4 graphically illustrates A1c (μmol/L) versus intralipid concentration (mg/dL) results obtained using intralipid spiked whole blood (6.5% and 8% HbA1c).
Figure 5:
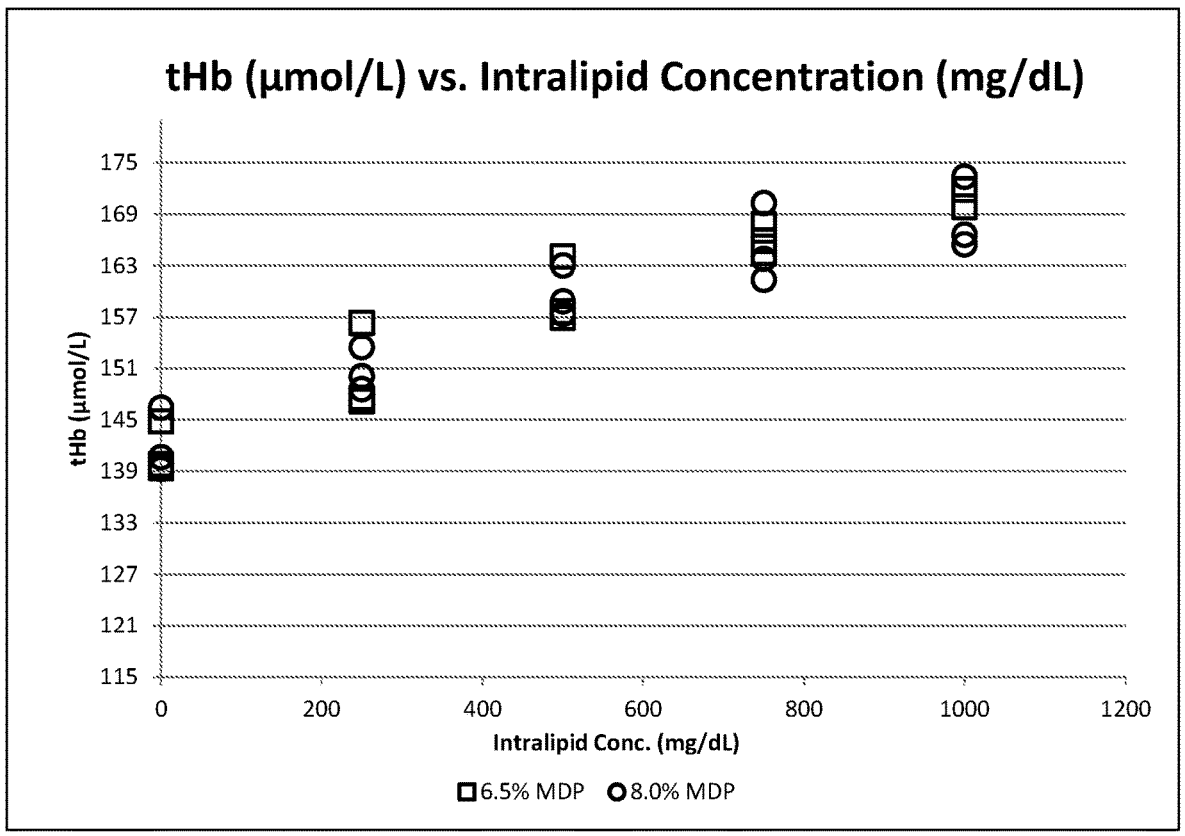
FIG. 5 graphically illustrates total hemoglobin (tHb; μmol/L) versus intralipid concentration (mg/dL) results obtained using intralipid spiked whole blood (6.5% and 8% HbA1c).
Figure 6:
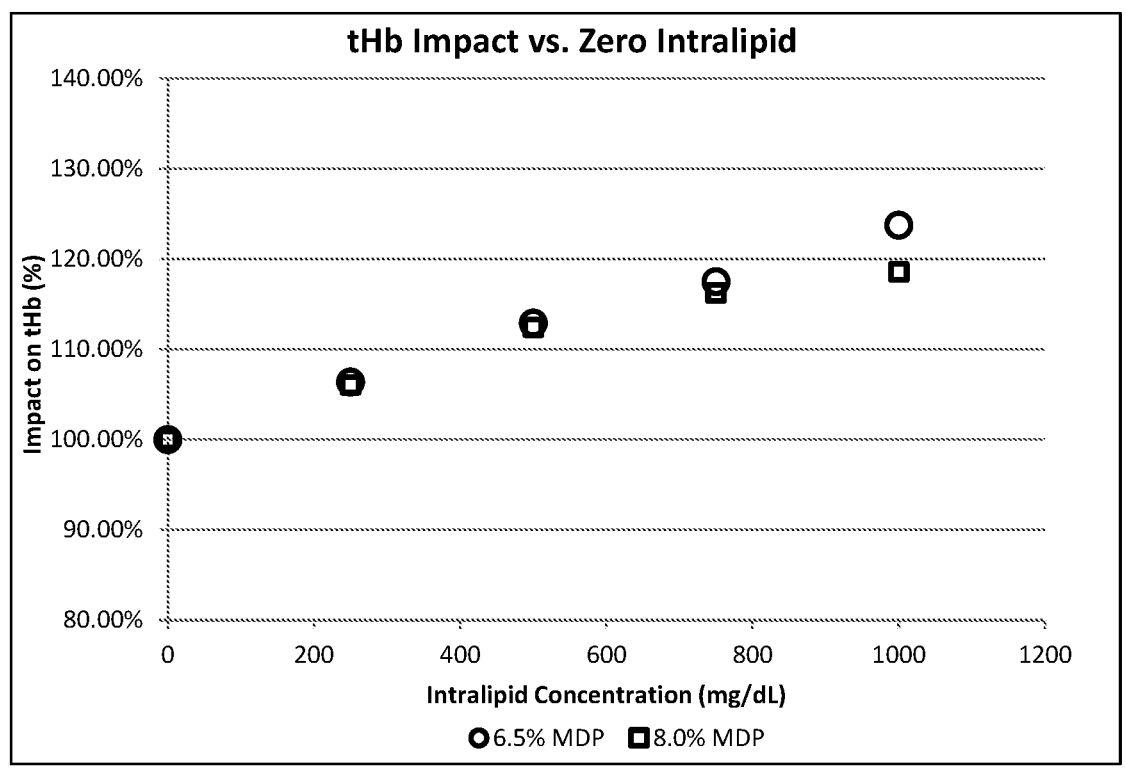
FIG. 6 graphically illustrates the impact of increasing intralipid on tHb (%) versus absence of intralipid.

Similar to the previous assay platform, the impact of intralipid interference and sample turbidity on the current glycated hemoglobin assay is exhibited on the tHb portion. Therefore, a turbidity normalization equation is also necessary for this platform (FIG. 4, FIG. 5, and FIG. 6 and Table II).

TABLE II

Impact of Increasing Intralipid on A1c (%) and tHb (%) versus Zero Intralipid

| Sample | Intralipid Conc. | A1c 658/805 (μmol/L) | Average A1c | tHb-Blank 478-694 (μmol/L) | Average tHb | A1c Impact vs. Zero Intralipid | tHb Impact vs. Zero Intralipid |
|---|---|---|---|---|---|---|---|
| 6.5% MDP | 0 | 6.65 | 6.80 | 139.40 | 141.35 | 100.00% | 100.00% |
| | | 6.73 | | 139.82 | | | |
| | | 7.01 | | 144.82 | | | |
| | 250 | 6.64 | 6.80 | 147.16 | 150.36 | 100.10% | 106.37% |
| | | 6.68 | | 147.55 | | | |
| | | 7.09 | | 156.36 | | | |
| | 500 | 6.66 | 6.81 | 156.96 | 159.57 | 100.25% | 112.90% |
| | | 6.79 | | 157.68 | | | |
| | | 6.99 | | 164.08 | | | |
| | 750 | 6.79 | 6.74 | 165.91 | 166.07 | 99.22% | 117.49% |
| | | 6.66 | | 164.50 | | | |
| | | 6.78 | | 167.81 | | | |

TABLE II-continued

Impact of Increasing Intralipid on A1c (%) and tHb (%) versus Zero Intralipid

| Sample | Intralipid Conc. (µmol/L) | A1c 658/805 (µmol/L) | Average A1c | tHb-Blank 478-694 (µmol/L) | Average tHb | A1c Impact vs. Zero Intralipid | tHb Impact vs. Zero Intralipid |
|---|---|---|---|---|---|---|---|
| | 1000 | 6.74 | 6.96 | 169.86 | 174.90 | 102.45% | 123.74% |
| | | 6.82 | | 171.87 | | | |
| | | 7.33 | | 182.97 | | | |
| 8.0% MDP | 0 | 8.84 | 9.03 | 139.25 | 142.09 | 100.00% | 100.00% |
| | | 8.97 | | 140.64 | | | |
| | | 9.27 | | 146.39 | | | |
| | 250 | 8.96 | 8.95 | 148.57 | 150.69 | 99.19% | 106.05% |
| | | 8.94 | | 150.05 | | | |
| | | 8.96 | | 153.46 | | | |
| | 500 | 9.05 | 9.13 | 158.86 | 159.77 | 101.18% | 112.44% |
| | | 9.05 | | 157.41 | | | |
| | | 9.30 | | 163.03 | | | |
| | 750 | 8.90 | 9.09 | 161.36 | 165.15 | 100.70% | 116.23% |
| | | 9.01 | | 163.79 | | | |
| | | 9.36 | | 170.30 | | | |
| | 1000 | 8.82 | 9.00 | 165.49 | 168.48 | 99.70% | 118.57% |
| | | 9.26 | | 173.35 | | | |
| | | 8.92 | | 166.61 | | | |

Not all clinical chemistry analyzers on which glycated hemoglobin assays are performed have a filter at 884 nm; therefore, the glycation hemoglobin assay described herein includes recalculation of the tHb and cHb testing wavelengths along with the tHb normalization constants to allow for performance on other analyzers (such as, but not limited to, the Atellica CH module, Siemens Healthineers, Tarrytown, N.Y.). The A1c testing wavelengths use by this glycated hemoglobin assay remain the same at 658/805 nm. The tHb testing wavelengths used in the current assay are 478/694 nm, and the cHb testing wavelength used in the current assay is 805 nm.

The following protocol describes the process that was used to optimize the parameters of the glycated hemoglobin assay of the present disclosure.

Whole blood Medical Decision Pools, valued at 5.0, 6.5, 8.0, and 12.0% HbA1c, were used in multiple feasibility studies. These samples were made as follows. Fresh site draw samples were collected and spiked with High BBI material (Hemoglobin A1C HbA1C, SKU P186-0B; BBI Solutions, Crumlin, UK) to obtain the targeted % HbA1c values mentioned above. The samples were value assigned on the Tosoh G8 HPLC analyzer (Tosoh Bioscience, Inc., South San Francisco, Calif.; SN 13523607). Samples were pipetted into 0.5 mL aliquots and frozen.

Figure 7:
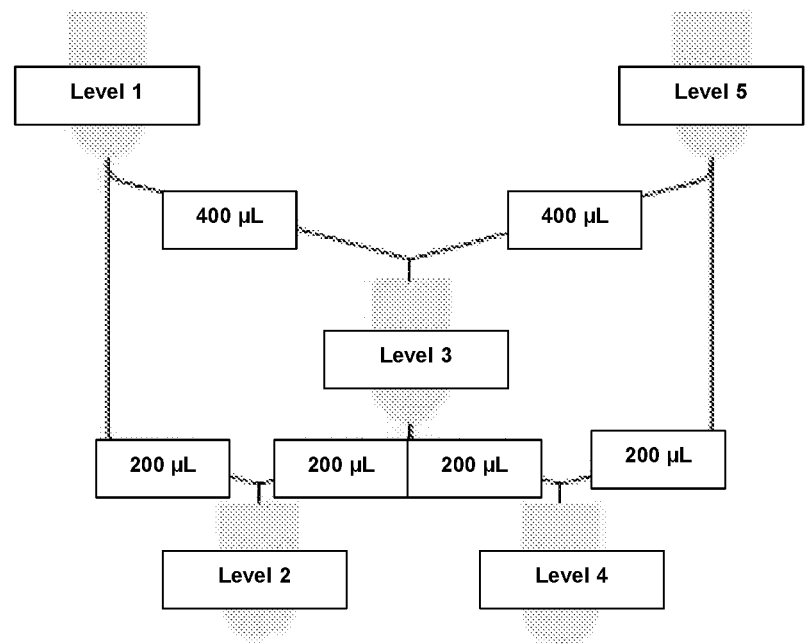
FIG. 7 illustrates a dilution scheme for intralipid spiked samples.

A linear regression was used to evaluate the impact of intralipid on tHb concentrations at the new wavelength. Two mL of frozen whole blood MDP (Medical Decision Point) samples, valued at 6.5% HbA1c, were thawed and gently inverted for approximately one hour. 50 µL of intralipid at 20,000 mg/dL was spiked into 950 µL of the thawed MDP totaling one (1) mL whole blood sample with a final intralipid concentration of 1000 mg/dL. The mixture was inverted for approximately 30 minutes to ensure homogeneity. Five unique whole blood samples of increasing intralipid concentration (0 mg/dL, 250 mg/dL, 500 mg/dL, 750 mg/dL, and 1000 mg/dL) were then created using the dilution schematic illustrated in FIG. 7. Each level was then tested on the Atellica CH module in replicates of 3. Data was then plotted and the slope and y-intercept found via linear regression analysis.

Figure 8:
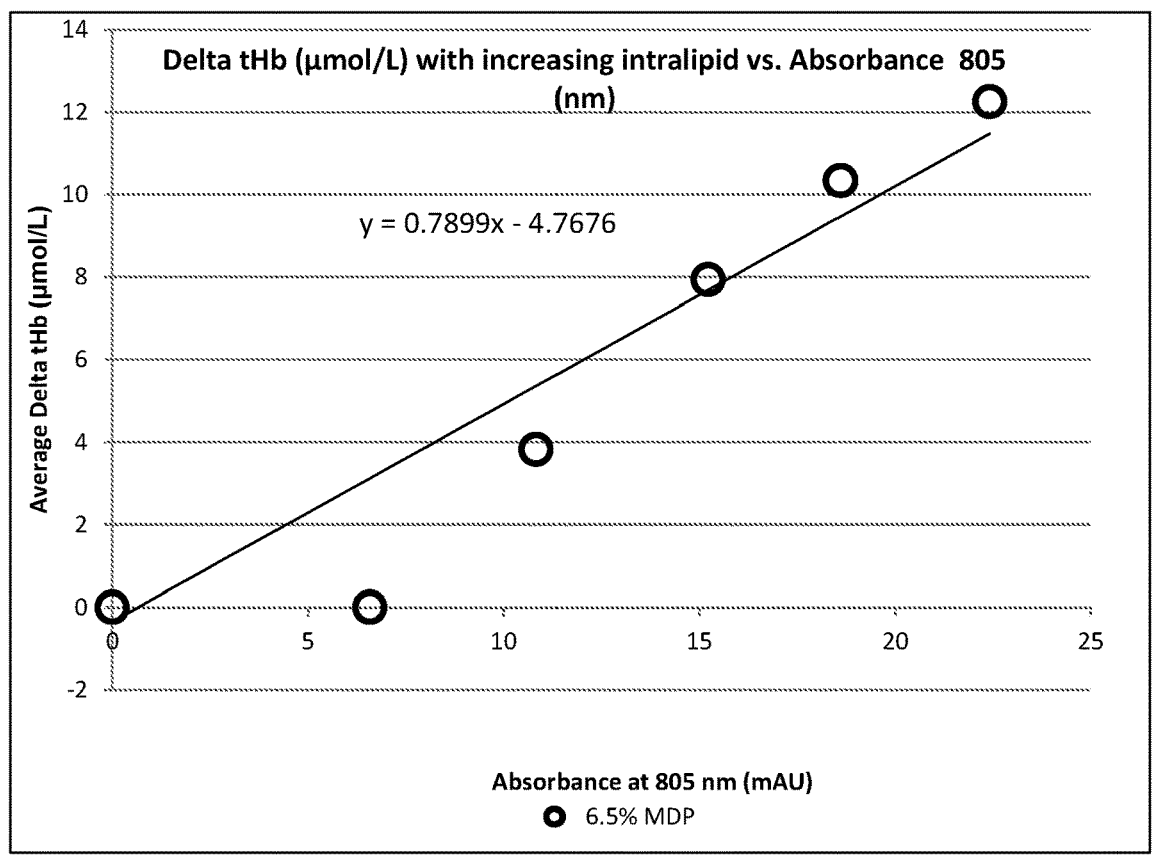
FIG. 8 graphically illustrates delta tHb (μmol/L) with increasing intralipid versus absorbance at 805 nm in whole blood (6.5% HbA1c) spiked with intralipid.

As shown in FIG. 8, the equation y=0.7899x−4.7676 was established via linear regression and its slope used to develop the new turbidity normalization equation.

Figure 9:
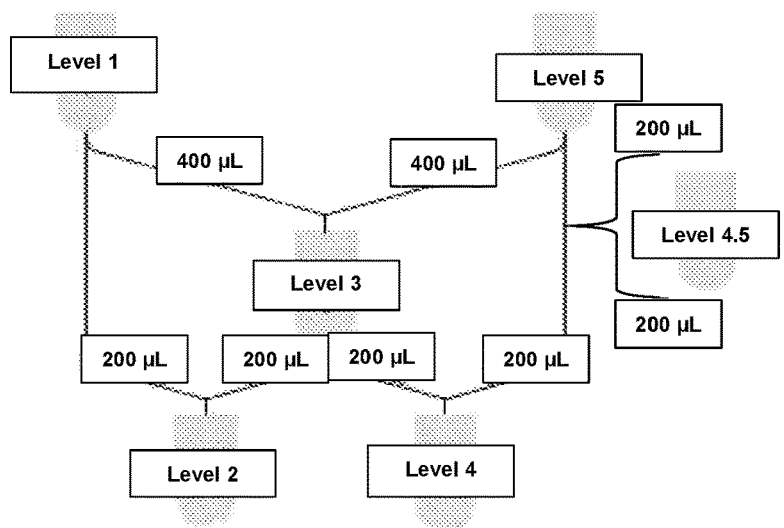
FIG. 9 illustrates a dilution scheme for normal samples.

A linear regression was used to evaluate the relationship of tHb concentration and absorbance at 805 nm. A hemolysate was made from a donor site draw totaling 10 mL of human whole blood. The EDTA tubes were allowed to sit refrigerated for >4 hours, and the cells and plasma naturally separate. The plasma was removed from each tube and transferred to a separate container. The red cells were then centrifuged at 2000 g for ten minutes to pack cells, and the supernatant was discarded. The packed cells were washed with saline and re-centrifuged three times, discarding the supernatant between each wash. The washed cells were frozen overnight at −70° C. and thawed the next day for testing. Equally spaced dilutions of plasma and a concentrated hemolysate 250 µmol/L tHb) were created, totaling six unique samples of increasing tHb concentration, following the dilution schematic shown in FIG. 9. The fifth and highest level 250 µmol/L tHb) was unable to be aspirated by the Atellica dilution probe, which alerted a viscosity sample delta flag; therefore, a 4.5 level was made using levels 4 and 5. Each level was then tested on the Atellica CH analyzer in replicates of 3. Data was then plotted and the slope and y-intercept found.

Figure 10:
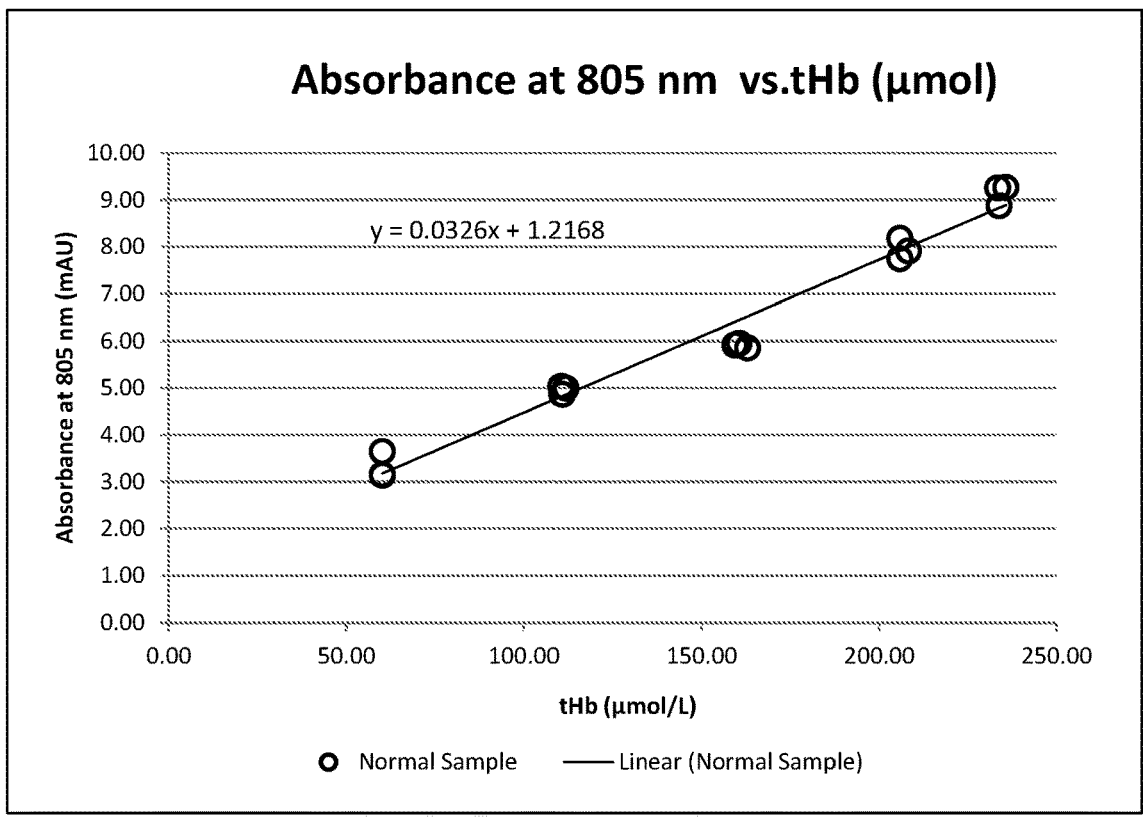
FIG. 10 graphically illustrates absorbance at 805 nm versus tHb (μmol) in normal samples diluted with saline.

As shown in FIG. 10, the equation y=0.0326x+1.2168 was established via linear regression, and its slope was used to develop the new turbidity normalization equation.

Using the slopes 0.7899 and 0.0326 from both experiments, the normalization equation was formulated as shown below:

Normalized tHb_E is calculated per Equation [1]:

$$\text{tHb\_E}_{norm} = \text{tHb\_E}_{not\text{-}norm} - \text{tHb\_E}_{turbidity} \quad [1]$$

Where tHb_E$_{norm}$ is the total hemoglobin after normalization (µmol/L); tHb_E$_{not\text{-}norm}$ is the total hemoglobin prior to normalization (µmol/L); and tHb_E$_{turbidity}$ is the turbidity contribution to tHb_E (µmol/L).

tHb_E$_{turbidity}$ is calculated per Equation [2a]. In equation [2a], absorbance at 805 nm (cHb) is used to determine the equivalent tHb contribution due to turbidity at the assay's read wavelength (478 nm). The second part of the equation (tHb_E$_{not\text{-}norm}$×0.0326) accounts for the true hemoglobin contribution at 884 nm and must be subtracted to determine the true turbidity contribution to tHb_E.

The 0.7899 and 0.0326 factors are empirically derived. 0.7899 is the slope of the linear regression of the change in total hemoglobin measured at 478 nm (tHb_$E_{notnorm}$) in samples with increasing turbidity (intralipid was used to spike whole blood to simulate lipemic sample conditions) versus Absorbance at 805 nm ($Abs_{805\ nm}$). 0.0326 is the slope of Absorbance at 884 nm versus increasing Hemoglobin concentration.

$$\text{tHb}\_E_{turbidity} = 0.7899 \times [Abs_{805\ nm} - (\text{tHb}\_E_{not\text{-}norm} \times 0.0326)] \quad [2a]$$

Equation [2a] simplifies to Equations [2b] and [2c].

$$\text{tHb}\_E_{turbidity} = (0.7899)(Abs_{805\ nm}) - (0.7899)(\text{tHb}\_E_{not\text{-}norm})(0.0326) \quad [2b]$$

$$\text{tHb}\_E_{turbidity} = (0.7899)(Abs_{805\ nm}) - (0.03)(\text{tHb}\_E_{not\text{-}norm}) \quad [2c]$$

Substituting equation [2c] back into equation [1] yields equation [3a]:

$$\text{tHb}\_E_{norm} = \text{tHb}\_E_{not\text{-}norm} - ((0.7899)(Abs_{805\ nm}) - (0.03)(\text{tHb}\_E_{not\text{-}norm})) \quad [3a]$$

Equation [3a] then simplifies to [3b] and [3c]:

$$\text{tHb}\_E_{norm} = \text{tHb}\_E_{not\text{-}norm} - (0.7899)(Abs_{805\ nm}) + (0.03)(\text{tHb}\_E_{not\text{-}norm}) \quad [3b]$$

$$\text{tHb}\_E_{norm} = (1.03)(\text{tHb}\_E_{not\text{-}norm}) - (0.7899)(Abs_{805\ nm}) \quad [3c]$$

Final Normalization equation:

$$\text{Normalized tHb}\_E = 1.03 \times \text{tHb}\ (\mu mol/L) - cHb\ (Abs_{805\ nm}) \times 0.7899$$

To evaluate the wavelengths, 2 mL of frozen whole blood MDP samples valued at 6.5% HbA1c were thawed and gently inverted for approximately one hour. 50 μL of intralipid at 20,000 mg/dL was spiked into 950 μL of the thawed MDP totaling one (1) mL whole blood sample with a final intralipid concentration of 1000 mg/dL. The mixture was inverted for approximately 30 minutes to ensure homogeneity. The control samples (MDPs without intralipid) and the test samples (intralipid spiked MDPs) were tested on the analyzer in replicates of 3. Interference (Dobs) and % Bias were calculated and evaluated for the following combination of wavelengths: (1) A1c—658/805 nm and tHb—478/805 nm, as shown in Table III; (2) A1c—658/694 nm and tHb—478/694 nm, as shown in Table IV; (3) A1c—658/694 nm and tHb—478/805 nm, as shown in Table V; and (4) A1c—658/805 nm and tHb—478/694 nm, as shown in Table VI. The testing wavelengths 658/805 nm for A1c and 478/694 nm for tHb (Table VI) showed the best performance and were therefore established as the new testing wavelengths.

TABLE III

Intralipid Spiked Samples Measured at 658/805 nm (A1c) and 478/805 nm (tHb)

| SID | Replicate | A1c 658/805 (μmol/L) | tHb 478/805 (μmol/L) | % A1c | Average % A1c | Interference (Dobs) | % Bias |
|---|---|---|---|---|---|---|---|
| 6.5% Control | 1 | 6.66 | 146.97 | 6.30 | 6.34 | | |
| | 2 | 6.75 | 147.28 | 6.34 | | | |
| | 3 | 7.02 | 152.07 | 6.38 | | | |
| 6.5% Test | 1 | 6.75 | 161.57 | 5.97 | 5.99 | −0.35 | −5.52% |
| | 2 | 6.84 | 163.71 | 5.97 | | | |
| | 3 | 7.34 | 173.60 | 6.02 | | | |
| 8.0% Control | 1 | 8.86 | 145.84 | 7.71 | 7.71 | | |
| | 2 | 8.99 | 147.40 | 7.73 | | | |
| | 3 | 9.29 | 153.19 | 7.70 | | | |
| 8.0% Test | 1 | 8.84 | 158.33 | 7.26 | 7.29 | −0.43 | −5.55% |
| | 2 | 9.29 | 164.90 | 7.31 | | | |
| | 3 | 8.94 | 159.14 | 7.29 | | | |

TABLE IV

Intralipid Spiked Samples Measured at 658/694 nm (A1c) and 478/694 nm (tHb)

| SID | Replicate | A1c 658/694 (μmol/L) | tHb 478/694 (μmol/L) | % A1c | Average % A1c | Interference (Dobs) | % Bias |
|---|---|---|---|---|---|---|---|
| 6.5% Control | 1 | 6.65 | 139.98 | 6.50 | 6.52 | | |
| | 2 | 6.73 | 140.35 | 6.54 | | | |
| | 3 | 6.96 | 145.38 | 6.53 | | | |
| 6.5% Test | 1 | 6.77 | 149.44 | 6.30 | 6.27 | −0.25 | −3.90% |
| | 2 | 6.78 | 151.51 | 6.25 | | | |
| | 3 | 7.23 | 160.90 | 6.26 | | | |
| 8.0% Control | 1 | 8.90 | 139.64 | 7.98 | 7.95 | | |
| | 2 | 8.93 | 141.19 | 7.94 | | | |
| | 3 | 9.30 | 146.94 | 7.94 | | | |
| 8.0% Test | 1 | 8.84 | 146.59 | 7.67 | 7.64 | −0.32 | −3.98% |
| | 2 | 9.13 | 153.29 | 7.60 | | | |
| | 3 | 8.85 | 147.41 | 7.64 | | | |

TABLE V

Intralipid Spiked Samples Measured at 658/694 nm (A1c) and 478/805 nm (tHb)

| SID | Replicate | A1c 658/694 (μmol/L) | tHb 478/805 (μmol/L) | % A1c | Average % A1c | Interference (Dobs) | % Bias |
|---|---|---|---|---|---|---|---|
| 6.5% Control | 1 | 6.65 | 146.97 | 6.29 | 6.32 | | |
|  | 2 | 6.73 | 147.28 | 6.33 | | | |
|  | 3 | 6.96 | 152.07 | 6.34 | | | |
| 6.5% Test | 1 | 6.77 | 161.57 | 5.99 | 5.96 | −0.36 | −5.67% |
|  | 2 | 6.78 | 163.71 | 5.94 | | | |
|  | 3 | 7.23 | 173.60 | 5.96 | | | |
| 8.0% Control | 1 | 8.90 | 145.84 | 7.73 | 7.71 | | |
|  | 2 | 8.93 | 147.40 | 7.69 | | | |
|  | 3 | 9.30 | 153.19 | 7.71 | | | |
| 8.0% Test | 1 | 8.84 | 158.33 | 7.26 | 7.24 | −0.47 | −6.13% |
|  | 2 | 9.13 | 164.90 | 7.22 | | | |
|  | 3 | 8.85 | 159.14 | 7.24 | | | |

TABLE VI

Intralipid Spiked Samples Measured at 658/805 nm (A1c) and 478/694 nm (tHb)

| SID | Replicate | A1c 658/805 (μmol/L) | tHb 478/694 (μmol/L) | % A1c | Average % A1c | Interference (Dobs) | % Bias |
|---|---|---|---|---|---|---|---|
| 6.5% Control | 1 | 6.66 | 139.98 | 6.50 | 6.54 | | |
|  | 2 | 6.75 | 140.35 | 6.55 | | | |
|  | 3 | 7.02 | 145.38 | 6.57 | | | |
| 6.5% Test | 1 | 6.75 | 149.44 | 6.28 | 6.30 | −0.24 | −3.74% |
|  | 2 | 6.84 | 151.51 | 6.28 | | | |
|  | 3 | 7.34 | 160.90 | 6.33 | | | |
| 8.0% Control | 1 | 8.86 | 139.64 | 7.96 | 7.96 | | |
|  | 2 | 8.99 | 141.19 | 7.98 | | | |
|  | 3 | 9.29 | 146.94 | 7.94 | | | |
| 8.0% Test | 1 | 8.84 | 146.59 | 7.67 | 7.69 | −0.27 | −3.37% |
|  | 2 | 9.29 | 153.29 | 7.70 | | | |
|  | 3 | 8.94 | 147.41 | 7.70 | | | |

All the following feasibility data employed the new normalization equation during analysis.

Figure 11:
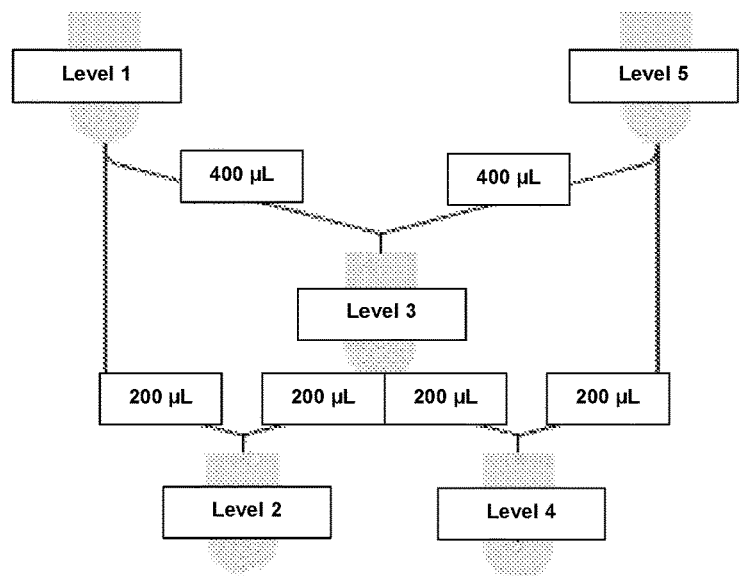
FIG. 11 illustrates a dilution scheme used for Atellica CH-intralipid interference.

Two mL of frozen whole blood MDP samples valued at 6.5% & 8.0% HbA1c were thawed and gently inverted for approximately one hour. 50 μL of intralipid at 20,000 mg/dL was spiked into 950 μL of the thawed 6.5% MDP to reach a final intralipid concentration of 1000 mg/dL in one (1) mL of whole blood. 50 μL of intralipid at 20,000 mg/dL was spiked into 950 μL of the thawed 8.0% MDP to reach a final intralipid concentration of 1000 mg/dL in one (1) mL of whole blood. The mixtures were inverted for approximately 30 minutes to ensure homogeneity. Five unique whole blood samples of increasing intralipid concentration (0 mg/dL, 250 mg/dL, 500 mg/dL, 750 mg/dL, and 1000 mg/dL) were then created for both levels of MDPs using the dilution schematic illustrated in FIG. 11. Each level was then tested on the Atellica CH analyzer in replicates of three, and the average and % bias were calculated, as shown in Table VII and Table VIII.

TABLE VII

Intralipid Interference and Dose Response Without Normalization

| MDP (% A1c) | Intralipid Conc (mg/dL) | Mean (% A1c) | Intralipid % Bias |
|---|---|---|---|
| 6.50% | 0 | 6.55 | |
|  | 250 | 6.29 | −4% |
|  | 500 | 6.06 | −8% |
|  | 750 | 5.87 | −10% |
|  | 1000 | 5.79 | −12% |
| 8.50% | 0 | 7.96 | |
|  | 250 | 7.59 | −5% |
|  | 500 | 7.38 | −7% |
|  | 750 | 7.19 | −10% |
|  | 1000 | 7.04 | −12% |

TABLE VIII

Intralipid Interference and Dose Response With Normalization

| MDP (% A1c) | Intralipid Conc (mg/dL) | Mean (% A1c) | Intralipid % Bias |
|---|---|---|---|
| 6.50% | 0 | 6.53 | |
|  | 250 | 6.43 | −2% |
|  | 500 | 6.32 | −3% |
|  | 750 | 6.24 | −4% |
|  | 1000 | 6.28 | −4% |

TABLE VIII-continued

Intralipid Interference and Dose Response With Normalization With Normalization

| MDP (% A1c) | Intralipid Conc (mg/dL) | Mean (% A1c) | Intralipid % Bias |
|---|---|---|---|
| 8.50% | 0 | 7.94 | |
| | 250 | 7.76 | −2% |
| | 500 | 7.70 | −3% |
| | 750 | 7.66 | −4% |
| | 1000 | 7.67 | −3% |

As can be seen, intralipid interference is not impactful in the new glycated hemoglobin assays of the present disclosure, and the resulting % bias is below the specified target, |+/−5%|, when measured at the target intralipid concentration (1000 mg/dL).

Thus, in accordance with the present disclosure, there have been provided compositions and methods of producing and using same which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A method of measuring percent glycated hemoglobin or a glycated hemoglobin:total hemoglobin ratio in a biological sample, the method comprising the steps of:
   (i) measuring absorbance at a first wavelength and a second wavelength in a biological sample containing lysed red blood cells and determining a total hemoglobin concentration (tHb) based on the measurements obtained at these two wavelengths, wherein the first wavelength is 658 nm, and wherein the second wavelength is in a range of from about 689 nm to about 699 nm;
   (ii) measuring absorbance at a third wavelength and a fourth wavelength in the biological sample containing lysed red blood cells and determining a glycated hemoglobin concentration (A1c) based on the measurements obtained at these two wavelengths, wherein the third wavelength is 658 nm, and wherein the fourth wavelength is in a range of from about 785 nm to about 825 nm;
   (iii) normalizing the total hemoglobin concentration calculated in (i) utilizing the absorbance measured at the fourth wavelength (cHb) in step (ii) and a turbidity normalization algorithm to substantially remove any turbidity interference from the wavelength measurements of (i), wherein any turbidity interference is substantially reduced to less than +/−about 5% at an intralipid concentration of up to about 1000 mg/dL, and wherein the turbidity normalization algorithm is: Normalized tHb=1.03×tHb (μmol/L)−cHb×0.7899; and
   (iv) calculating a percent glycated hemoglobin or glycated hemoglobin:total hemoglobin ratio based on the concentrations calculated in (ii) and (iii).

2. The method of claim 1, wherein the biological sample is a lysed whole blood sample.

3. The method of claim 1, wherein the steps are performed in a single reaction cuvette.

4. The method of claim 1, wherein the second wavelength is 694 nm, and the fourth wavelength is 805 nm.

5. A method of measuring percent glycated hemoglobin or a glycated hemoglobin:total hemoglobin ratio in a biological sample, the method comprising the steps of:
   (a) lysing red blood cells present in the biological sample;
   (b) reacting the lysed red blood cells with a reagent to oxidize hemoglobin to methemoglobin;
   (c) cleaving an N-terminal fructosyl dipeptide fragment from the hemoglobin beta chain with a protease;
   (d) converting methemoglobin into azide-methemoglobin;
   (e) measuring absorbance at a first wavelength and a second wavelength and determining a total hemoglobin concentration (tHb) based on the measurements obtained at these two wavelengths, wherein the first wavelength is 658 nm, and wherein the second wavelength is in a range of from about 689 nm to about 699 nm;
   (f) reacting the N-terminal fructosyl peptide fragment with a reagent to generate hydrogen peroxide;
   (g) measuring absorbance at a third wavelength and a fourth wavelength and determining a glycated hemoglobin concentration (A1c) based on the measurements obtained at these two wavelengths, wherein the third wavelength is 658 nm, and wherein the fourth wavelength is in a range of from about 785 nm to about 825 nm;
   (h) normalizing the total hemoglobin concentration calculated in step (e) utilizing the absorbance measured at the fourth wavelength (cHb) in step (g) and a turbidity normalization algorithm to substantially remove any turbidity interference from the wavelength measurements of step (e); and
   (i) calculating a percent glycated hemoglobin or glycated hemoglobin:total hemoglobin ratio based on the concentrations calculated in steps (g) and (h).

6. The method of claim 5, wherein the turbidity normalization algorithm used in step (h) is: Normalized tHb=1.03× tHb (μmol/L)−cHb×0.7899.

7. The method of claim 5, wherein the biological sample is a whole blood sample.

8. The method of claim 5, wherein steps (a)-(g) are performed in a single reaction cuvette.

9. The method of claim 5, wherein the second wavelength is 694 nm, and the fourth wavelength is 805 nm.

10. The method of claim 5, wherein the reagent used to oxidize hemoglobin to methemoglobin in step (b) is sodium nitrite.

11. The method of claim 5, wherein in step (d), methemoglobin is converted into azide-methemoglobin in the presence of sodium azide.

12. The method of claim 5, wherein the reagent used in step (f) is fructosyl peptide oxidase.

13. The method of claim 5, wherein any turbidity interference is substantially reduced to less than +/−about 5% at an intralipid concentration of up to about 1000 mg/dL.

14. A method of measuring percent glycated hemoglobin or a glycated hemoglobin:total hemoglobin ratio in a biological sample, the method comprising the steps of:
   (a) lysing red blood cells present in the biological sample;
   (b) reacting the lysed red blood cells with sodium nitrite to oxidize hemoglobin to methemoglobin;
   (c) cleaving an N-terminal fructosyl dipeptide fragment from the hemoglobin beta chain with a protease;
   (d) converting methemoglobin into azide-methemoglobin in the presence of sodium azide;

(e) measuring absorbance at a first wavelength and a second wavelength and determining a total hemoglobin concentration (tHb) based on the measurements obtained at these two wavelengths, wherein the first wavelength is 658 nm, and wherein the second wavelength is in a range of from about 689 nm to about 699 nm;

(f) reacting the N-terminal fructosyl peptide fragment with a reagent to generate hydrogen peroxide;

(g) measuring absorbance at a third wavelength and a fourth wavelength and determining a glycated hemoglobin concentration (A1c) based on the measurements obtained at these two wavelengths, wherein the third wavelength is 658 nm, and wherein the fourth wavelength is in a range of from about 785 nm to about 825 nm;

(h) normalizing the total hemoglobin concentration calculated in step (e) utilizing the absorbance measured at the fourth wavelength (cHb) in step (g) and a turbidity normalization algorithm to substantially remove any turbidity interference from the wavelength measurements of step (e), wherein any turbidity interference is substantially reduced to less than +/−about 5% at an intralipid concentration of up to about 1000 mg/dL, and wherein the turbidity normalization algorithm is: Normalized tHb=1.03×tHb (µmol/L)−cHb×0.7899; and (i) calculating a percent glycated hemoglobin or glycated hemoglobin:total hemoglobin ratio based on the concentrations calculated in steps (g) and (h).

15. The method of claim 14, wherein the biological sample is a whole blood sample.

16. The method of claim 14, wherein steps (a)-(g) are performed in a single reaction cuvette.

17. The method of claim 14, wherein the second wavelength is 694 nm, and the fourth wavelength is 805 nm.

* * * * *

UNITED STATES PATENT AND TRADEMARK OFFICE
CERTIFICATE OF CORRECTION

| | |
|---|---|
| PATENT NO. | : 11,300,577 B1 |
| APPLICATION NO. | : 17/310033 |
| DATED | : April 12, 2022 |
| INVENTOR(S) | : Justine Jones, Jian Dai and Candice Robinson |

It is certified that error appears in the above-identified patent and that said Letters Patent is hereby corrected as shown below:

In the Specification

Column 5, Line 62: Delete "first wavelength is 658 nm" and replace with --first wavelength is 478 nm--

Column 6, Line 55: Delete "first wavelength is 658 nm" and replace with --first wavelength is 478 nm--

Column 8, Lines 10-11: Delete "first wavelength is 658 nm" and replace with --first wavelength is 478 nm--

In the Claims

Column 17, Lines 39-40: Delete "first wavelength is 658 nm" and replace with --first wavelength is 478 nm--

Column 18, Lines 25-26: Delete "first wavelength is 658 nm" and replace with --first wavelength is 478 nm--

Column 19, Lines 4-5: Delete "first wavelength is 658 nm" and replace with --first wavelength is 478 nm--

Signed and Sealed this
Fourth Day of October, 2022

Katherine Kelly Vidal
*Director of the United States Patent and Trademark Office*